(12) United States Patent
Groenlund et al.

(10) Patent No.: US 8,454,964 B2
(45) Date of Patent: Jun. 4, 2013

(54) MICROPARTICLES COMPRISING CARBOHYDRATE BEADS COVALENTLY LINKED WITH ALLERGEN

(75) Inventors: Hans Groenlund, Lidingoe (SE); Johan Roennelid, Uppsala (SE); Alex Karlsson-Parra, Moelndal (SE); Marianne Van Hage-Hamsten, Bromma (SE); Rudolf Valenta, Theresienfeld (AT); Susanne Vrtala, Vienna (AT); Ursula Wiedermann, Vienna (AT); Dietrich Kraft, Vienna (AT)

(73) Assignee: Biomay AG, Vienna (AT)

( * ) Notice: Subject to any disclaimer, the term of this patent is extended or adjusted under 35 U.S.C. 154(b) by 735 days.

(21) Appl. No.: 10/510,655

(22) PCT Filed: Apr. 17, 2003

(86) PCT No.: PCT/EP03/04103
§ 371 (c)(1),
(2), (4) Date: Nov. 30, 2004

(87) PCT Pub. No.: WO03/089009
PCT Pub. Date: Oct. 30, 2003

(65) Prior Publication Data
US 2005/0095298 A1    May 5, 2005

(30) Foreign Application Priority Data
Apr. 22, 2002 (EP) .................................. 02008283

(51) Int. Cl.
| A61K 39/00 | (2006.01) |
| A61K 39/35 | (2006.01) |
| A61K 39/36 | (2006.01) |
| A61K 39/38 | (2006.01) |
| C07K 1/00 | (2006.01) |
| C07K 14/00 | (2006.01) |

(52) U.S. Cl.
USPC ..................... 424/184.1; 424/275.1; 530/350

(58) Field of Classification Search
None
See application file for complete search history.

(56) References Cited

U.S. PATENT DOCUMENTS

| 7,129,222 B2 * | 10/2006 | Van Nest et al. ............ 514/44 A |
| 2002/0055477 A1 * | 5/2002 | Nest et al. ................... 514/44 |

FOREIGN PATENT DOCUMENTS

| EP | 0 451 800 A1 | 10/1991 |
| WO | 84/00294 A1 | 2/1984 |
| WO | 95/19437 A1 | 7/1995 |
| WO | 98/43657 A2 | 10/1998 |

OTHER PUBLICATIONS

King et al. 'Demonstration of reaginic antibodies on human basophils by immune adherence to allergen-coated Sepharose beads.' Clin. Allergy 6(4):339-348, 1976.*
Nordvall et al. 'Timothy-specific IgG antibody levels vary with the pollen seasons.' Allergy 41(8):575-580, 1986.*
van Toorenenbergen et al. 'Immunoblot Analysis of IgE-Binding Antigens of Paprika and Tomato Pollen.' Int. Arch. Allergy Immunol. 122:246-250, 2000.*
Johansen et al. 'Revisiting PLA/PLGA microspheres: an analysis of their potential in parenteral vaccination.' Eur. J. Pharm. Biopharm. 50:129-146, 2000.*
Gronlund et al. 'Carbohydrate-based particles: a new adjuvant for allergen-specific immunotherapy.' Immunology 107:523-529, 2002.*
Neimert-Anderson et al. 'Carbohydrate-based particles reduce allergic inflammation in a mouse model for cat allergy.' Allergy 63:518-526, 2008.*
Kovacsovics-Bankowski et al. 'Efficient major histocompatibility complex class I presentation of exogenous antigen upon phagocytosis by macrophages.' Proc. Natl. Acad. Sci. 90:4942-4946, 1993.*
Sobotka et al. 'Allergy to insect stings IV.Diagnosis by Radioallergosorbent Test (R.A.S.T.)' J. Immunol. 121(6):2477-2484, 1976.*
Van Ree et al. 'How far can we simplify in vitro diagnostics for grass pollen allergy?: A study with 17 whole pollen extracts and purified natural and recombinant major allergens.' J. Allergy Clin. Immunol. 102:184-190, 1998.*
Harlow E, Lane, D. Antibodies a laboratory manual. Cold Spring Harbor, New York: Cold Spring Harbor Laboratory Press, Chapter 5: 53-137, 1989.*
US 5,849,884, 12/1998, Woiszwillo et al. (withdrawn).
N. Sai Geeta et al., "In vitro immunization of murine lymphocytes using immobilized immunogens", Biotechnol. Appl. Biochem., 1996, pp. 61-64, vol. 24.
Gabriele Schramm et al., "Allergen Engineering": Variants of the Timothy Grass Pollen Allergen Phl p 5b with Reduced IgE-Binding Capacity but Conserved T Cell Reactivity, The Journal of Immunology, 1999, pp. 2406-2414, vol. 162, No. 4.
Pauli, Gabrielle et al., J. Allergy & Clinical Immunology, vol. 122(5): pp. 951-960 (Nov. 2008).
Himly, Martin et al., FASEB Journal, 10.1096/fj.02-0472fje (Nov. 15, 2002).
D. Kraft et al., "The Importance of Recombinant Allergens for Diagnosis and Therapy of IgE-Mediated Allergies", Int Arch Allergy Immunol, (1999) vol. 118: 171-176 (Abstract Only).
R. Valenta et al., "Recombinant Allergens for Immunology", J Allergy Clin Immunol (2007), vol. 119 (4): 826-830 (Abstract Only).

* cited by examiner

*Primary Examiner* — Nora Rooney
(74) *Attorney, Agent, or Firm* — Chalin A. Smith; Smith Patent Consulting (57) ABSTRACT

Microparticles are disclosed which comprise a bead essentially consisting of a cross-linked carbohydrate and an antigen covalently linked thereto. The microparticle can be used for the treatment of disorders of the immune system and in diagnostic tests.

8 Claims, 4 Drawing Sheets

SEQUENCE LISTING

<160> NUMBER OF SEQ ID NOS: 1

<210> SEQ ID NO 1
<211> LENGTH: 284
<212> TYPE: PRT
<213> ORGANISM: Artificial Sequence
<220> FEATURE:
<223> OTHER INFORMATION: rPhl p 5b
<300> PUBLICATION INFORMATION:
<301> AUTHORS: Bufe, A. et al.
<302> TITLE: Major Allergen Phl p Vb in Timothy Grass is Novel Pollen RNase
<303> JOURNAL: FEBS Letters
<304> VOLUME: 363
<305> ISSUE: 1
<306> PAGES: 6-12
<307> DATE: 1995-04-17
<308> DATABASE ACCESSION NUMBER: Q40963
<309> DATABASE ENTRY DATE: 1997-11-01
<313> RELEVANT RESIDUES IN SEQ ID NO: (1)..(284)

<400> SEQUENCE: 1

```
Ala Ala Ala Ala Val Pro Arg Arg Gly Pro Arg Gly Gly Pro Gly Arg
1               5                   10                  15

Ser Tyr Thr Ala Asp Ala Gly Tyr Ala Pro Ala Thr Pro Ala Ala Ala
            20                  25                  30

Gly Ala Ala Ala Gly Lys Ala Thr Thr Glu Glu Gln Lys Leu Ile Glu
        35                  40                  45

Asp Ile Asn Val Gly Phe Lys Ala Ala Val Ala Ala Ala Ala Ser Val
    50                  55                  60

Pro Ala Ala Asp Lys Phe Lys Thr Phe Glu Ala Ala Phe Thr Ser Ser
65                  70                  75                  80

Ser Lys Ala Ala Ala Lys Ala Pro Gly Leu Val Pro Lys Leu Asp
                85                  90                  95

Ala Ala Tyr Ser Val Ala Tyr Lys Ala Ala Val Gly Ala Thr Pro Glu
                100                 105                 110

Ala Lys Phe Asp Ser Phe Val Ala Ser Leu Thr Glu Ala Leu Arg Val
            115                 120                 125

Ile Ala Gly Ala Leu Glu Val His Ala Val Lys Pro Val Thr Glu Glu
        130                 135                 140

Pro Gly Met Ala Lys Ile Pro Ala Gly Glu Leu Gln Ile Ile Asp Lys
145                 150                 155                 160

Ile Asp Ala Ala Phe Lys Val Ala Ala Thr Ala Ala Thr Ala Pro
                165                 170                 175

Ala Asp Asp Lys Phe Thr Val Phe Glu Ala Ala Phe Asn Lys Ala Ile
            180                 185                 190

Lys Glu Ser Thr Gly Gly Ala Tyr Asp Thr Tyr Lys Cys Ile Pro Ser
        195                 200                 205

Leu Glu Ala Ala Val Lys Gln Ala Tyr Ala Ala Thr Val Ala Ala Ala
    210                 215                 220

Pro Gln Val Lys Tyr Ala Val Phe Glu Ala Ala Leu Thr Lys Ala Ile
225                 230                 235                 240

Thr Ala Met Ser Glu Val Gln Lys Val Ser Gln Pro Ala Thr Gly Ala
                245                 250                 255

Ala Thr Val Ala Ala Gly Ala Ala Thr Thr Ala Ala Gly Ala Ala Ser
            260                 265                 270

Gly Ala Ala Thr Val Ala Ala Gly Gly Tyr Lys Val
        275                 280
```

MICROPARTICLES COMPRISING CARBOHYDRATE BEADS COVALENTLY LINKED WITH ALLERGEN

This application is a national stage of PCT/EP03/04103 filed Apr. 17, 2003. The entire contents of the above-identified application are hereby incorporated by reference.

The present invention relates to the field of immunotherapy and in particular to the treatment of patients suffering from allergic reactions against allergens, in particular allergens derived from plant pollen.

Allergen-specific immunotherapy which is mostly conducted by injecting allergen extracts into allergic patients was introduced many years ago. The occurrence of severe anaphylactic side effects caused by the injection of aqueous allergen extracts and the necessity to administer a great number of injections over long periods prompted the development of safe and efficacious allergen formulations. More than 60 years ago aluminium hydroxide-adsorbed allergen extracts were introduced for depot vaccination, showing improved immune stimulatory as well as reduced anaphylactic properties. Even today, aluminium hydroxide is by far the most common adjuvant used for injection immunotherapy.

Allergen-specific immunotherapy is one of the few known causative treatments of IgE-mediated allergy and numerous clinical studies document its clinical efficacy. Common clinical practise includes the subcutaneous injection of allergen extracts adsorbed to aluminium hydroxide with gradually increasing doses to a maintenance level and treatment periods up to 5 years or more. Aluminium hydroxide is preferred to other adjuvants (e.g., oil emulsions, liposome formulations) for injection immunotherapy of humans because it induces comparable little tissue reactions. Nevertheless aluminium hydroxide can cause local gramuloma formation at the injection sites. Other major disadvantages of aluminium hydroxide are the unpredictable efficacy of adsorption of certain allergens/allergen extracts, the unpredictable stability of the adsorbents, the possibility that allergens are altered in the course of the adsorption process and the difficulties in assessing quality and quantity of allergens once that they are adsorbed to aluminium hydroxide.

It is an object of the present invention to provide improved forms of antigens which can be used in particular for the treatment of patients suffering from allergic reactions.

The present invention discloses

Microparticles comprising
a) a bead essentially consisting of a carbohydrate and
b) an allergen which is covalently bound to the bead.

The carbohydrate bead consists essentially of a three-dimensionally linked Polymer which may be a polyarylamide, a vinyl polymer, a dextran or preferably agarose. Mixtures of the polymers can also be used. The carbohydrate-based particle consists of suitable polymer carbohydrates, preferably agarose which is linked in three dimensions. Suitable beads are commercially available, for example under the trademark Sepharose. The beads are small particles consisting of a gel-like carbohydrate which forms the support for the antigen. The microparticle consists of a carbohydrate-based bead which is covalently linked with an antigen at high density without dramatic alteration of its immunological properties.

The microparticles according to the present invention have a certain particle size which ranges from 0.1 µm to 10 µm and preferably from 0.5 µm to 5 µm. The size of the microparticles is essential. The size distribution means that the largest percentage, usually at least 80% of all beads are within the given range. Of course there are some beads outside this range since the diameter is distributed statistically. By applying special technique it is, however, possible to make sure that more than 99% of the beads are within the given range.

The microparticles of the present invention contain at least one antigen which is covalently linked to the carbohydrate bead. The antigen is a compound against which the immune-system of the animal or the human being to be immunized forms antibodies. The antigen may be any structure which forms an epitope. The antigen may be a polypeptide, a carbohydrate like for example glycosyl residues attached to a polypeptide or nucleic acids. In a preferred embodiment the antigen is an allergen which is derived from plant pollen. The surface structures of the plant pollen are the causative agents of allergic reactions. In preferred embodiments of the present invention the allergens are structures derived from grass pollen. In an especially preferred embodiment of the present invention the allergen is derived from timothy grass pollen.

The coupling of the carbohydrate-based beads to the antigen is based on the principle of forming a covalent bond between the carbohydrate backbone of the bead and a reactive group of the antigen. The covalent bond may be formed for example by a cyano bromide activation resulting in stable formation of amid bonds which can be applied for most proteins and peptides with high efficacy. Alternative binding methods which are well known in the art can be also used depending on the antigen to be bound to the bead.

In the experiments of the present application the antigen to be tested was purified recombinant Phlp 5b, a major timothy grass pollen allergen which was coupled to carbohydrate-based particles (CBP). In the examples the same antigen was only mixed with CBP (as comparative test) and in another comparative test the antigen was absorbed to aluminium hydroxide.

In the examples the Phlp 5b formulations were used to immunize mice and the levels, kinetics and profiles of antibody responses were analyzed.

In another set of experiments cytokine production in mouse spleen-cell-cultures was investigated and the injection sites were further analyzed by histopathology. The CBP–rPhl p 5b induced mouse antibodies were also tested for cross-reactivity to natural group 5 allergens from various grasses and their ability to inhibit the IgE-binding of grass pollen allergic patients to the allergen was studied.

It has been found that the microparticles of the present invention elicited comparable immune responses but less granulomatous tissue reactions than aluminium hydroxide. Therefore the microparticles do have less side-effects. Furthermore the antibodies induced by the microparticles of the present invention blocked allergic patients IgE-binding to rPhl p 5b which shows that the microparticles can be used successfully for the treatment of allergic patients.

The present invention discloses also a medicament for the treatment of the immune system which comprises microparticles according to the present invention. Such a medicament can be administered nasally, rectally or preferably parenterally. The microparticles can be included in suitable pharmaceutical formulations like solutions for injection, rectal foams or nasal sprays. It is also possible to prepare suitable ointments or plasters. The present invention provides also a diagnostic test system for the measurement of released cell mediators which comprises microparticles according to the present invention. One system is described in detail in example 2 and method 6.

The results of the present experiments show that the microparticles may represent a useful support and adjuvant for allergen-specific immunotherapy yielding comparable immune responses as aluminium hydroxide. The experiments show that purified rPhl p 5b allergen which is covalently bound to the carbohydrate-based bead induced strong IgG1, IgG2a/b and IgG3 antibody responses in mice. Those antibodies cross-reacted with natural group 5 allergens from all 5 grass species containing group 5 allergens and perhaps more important competed with the binding of grass pollen allergic patients IgE-antibodies to Phl p 5b. This finding suggests that the antibodies induced by the microparticles have the desirable features of blocking antibodies. Such blocking antibodies which are induced in the course of immunotherapy have beneficial effects as they can inhibit the allergen induced effect of cell activation and the IgE mediated presentation of allergens to T-cells.

The microparticles of the present invention offer several advantages compared to alternatively usable forms of imnunotherapy like, for example, the use of aluminium hydroxide.

Since the coupling of the antigen to the beads uses well described and reproducible procedures, it is exactly predictable which amount of antigen is loaded on the beads. Therefore the beads are covered with the antigen in high density, with a high yield and in a reproducible amount.

Another advantage can be seen in the fact that the antigens which are covalently conjugated to the beads are presented in a very efficient way by antigen presenting cells to the involved cells of the immunosystem. It can be concluded from the experiments which show that the cytokine response is much more vigorous in the group treated with microparticles of the present invention compared to the control group wherein the antigen was absorbed to aluminium that the cellular immune response is stimulated.

Another advantage is that the carbohydrate-based beads, in particular sepharose are highly bio-compatible. Therefore the vaccination formulations can be administered via different routes whereby the parenteral route is preferred. It is, however, also possible to administer the medicaments of the present invention by the oral, nasal, rectal or intra-venous administration. The subcutanous or intramuscular application is, however, preferred.

The following experiments show that the present microparticles are well tolerated when exposed to a variety of cell types in tissue culture and as column matrix in clinical ex-vivo treatments. This is in particular supported by the experiments which show that the immunisation of mice with the microparticles of the present invention induced less granulomatous reactions than the use of aluminium hydroxide under comparable treatment.

I) Methods
1) Patient Sera

Nine patients with a documented clinical history of allergy to timothy grass pollen, sensitised to rPhl p 5b and a timothy grass pollen RAST class value of 2 or higher were included in the study together with control sera.

2) Recombinant allergen cDNA coding for the major allergen rPhl p 5b was obtained by PCR according to the published rPhl p 5b sequence [Bufe et al. "Major allergen Phl p 5b in timothy grass is novel pollen RNase". FEBS Lett 1995;363:6-12.]. The Phi p 5b cDNA was subcloned into pET 17b (Novagen, Madison, Wis.) expressed, in *E coli* BL-21 (DE3) and purified to homogeneity as described [Vrtala et al. "Immunologic characterization of purified recombinant timothy grass pollen (*Phleum pretense*) allergens (Phi p 1, Phi p 2, Phi p 5)". J Allergy Clin Immunol 1996;97:781-7.].

3) Preparation of Conjugates and Adsorbates

Cyanogen bromide-activated spherical Sepharose particles (CBP), i.e. beaded agarose, with a mean diameter of 2.1 micrometer were provided by Pharmacia Diagnostics, Uppsala, Sweden. The beads were cyanogen bromide activated as described in the prior art [Axén et al. "Chemical coupling of peptides and proteins to polysaccharides by means of cyano halides". Nature 1967;214:1302-1304.]. Prior to conjugation 4 mg of lyophilized rPhl p 5b was dissolved in 8 ml 0.1 M carbonate-buffer pH 8.0 and added to 110 mg of activated particles in 2.0 ml 0.1 M carbonate-buffer pH 8.0. The allergen was conjugated to the particles by end-over-end mixing for 1 h at room temperature. CBP–rPhlp 5b were centrifuged at 1000×g for 5 min. Coupling efficiency was estimated to be >95% by measuring protein concentration by UV absorbance at 280 nm in supernatants before and after conjugation. Remaining active groups were blocked by resuspending the particles in 5 volumes of 0.1 M glycine pH 8.5 and incubated by end-over-end mixing for 1 hour. The gel was further washed by alternatively with 0.1 M sodium acetate, 1.0 M NaCl pH 4.0 and 0.1 M Tris, 1.0 M NaCl pH 8.0, 5 volumes each. Finally the CBP–rPhl p 5b was transferred to 50 mM phosphate buffer, 0.15 M NaCl, 10 mM EDTA 0.02% NaN$_3$, 0.05% Tween 20 pH 7.5 and stored at +4° C. until use. Stability of the covalent link between rPhl p 5b and CBP was confirmed after three months of storage at +4° C. by analysis of rPhl p5b in the supernatant. Aluminium hydroxide (Alum) adsorbates were prepared for comparative examples freshly prior to injection as described [Vrtala et al. "T cell epitope-containing hypoallergenic recombinant fragments of the major birch pollen allergen, Bet v 1, induce blocking antibodies". J Immunol 2000;165:6653-9.]. Briefly, aluminium hydroxide, AluGel-S (Serva, Heidelberg; Germany) was diluted 1:1 in PBS and mixed with rPhl p 5b to yield 5 μg per 100 μl gel.

4) Immunisation of Mice

Three groups, each consisting of five female 6-8 weeks old BALB/c mice (Charles River, Kislegg, Germany) were immunised with covalently bound CBP–rPhl p 5b (Group I), rPhl p 5b-Alum (Group II) as control and as a second control, rPhl p5b was mixed with CBP (group III).

The groups, treatment and time of immunisation are given in the following table I:

TABLE I

Groups of immunized mice

| Group | Treatment | Days of immunization | Day of sacrification |
|---|---|---|---|
| Group I | CBP – rPhl p 5b | 0, 28, 63, 121 | 128 |
| Group II | Alum – rPhl p 5b | 0, 28, 63, 121 | 128 |
| Group III | CBP + rPhl p 5b | 0, 28, 63, 121 | 128 |

The mice were immunised subcutaneously in the neck with 5 μg of rPhl p 5b in 100 μl of suspensions, from each of the three preparations. Immunisations were given and blood was taken on days 0, 28 and 63. On day 121 a booster injection was given and 7 days later the animals were sacrificed and spleen cells were prepared for cytokine measurements. The animals were kept in the animal care unit of the Department of Pathophysiology of the University of Vienna according to the local guidelines for animal care.

5) ELISA Detection of Allergen-Specific Antibodies

All 15 mice were bleed and antibodies IgG1, 2a/b, 3 and IgE specific to rPhl p 5b were analyzed individually in ELISA as described by [Vrtala et al. "Immunization with purified natural and recombinant allergens induces mouse IgG1 antibodies that recognize similar epitopes as human IgE, inhibit the human IgE-allergen interaction and allergen-induced basophil degranulation". J Immunol 1998;160:6137-40.].

Ninety-six well micro titre plates (Nunc, Roskilde, Denmark) were coated with 100 µl, 5 µg/ml rPhl p 5b in PBS over night at +4° C. The plates were washed 2 times with 0.05% Tween 20 in PBS (WB). To reduce unspecific binding, 200 µl WB-1% BSA was added for 2.5 h at room temperature. One hundred µl mouse serum diluted in WB-0.5% BSA, 1:1000 for IgG1, 1:100 for IgG2a/b and 3 and 1:20 for IgE respectively, was added per well and incubated over night at +4° C., followed by washing 5×250 µl with WB. One hundred µl rat anti-mouse IgG1, 2a/b, 3 and IgE (PharMingen, San Diego, Calif.) respectively, diluted 1:1000 in WB-0.5% BSA were incubated over night at +4° C. followed by washing. One hundred µl horseradish peroxidase labeled sheep anti-rat IgG diluted 1:1000 in WB-0.5% BSA, was incubated 2 h in room temperature followed by washing 5×250 µl with WB. ABTS (Sigma St Louis) was used as substrate and the colour reaction was read at 405 nin with a Dynatech microplate reader (Denkendorf, Germany).

Group 5 allergens in different grass pollen were detected by ELISA. Pollen allergen extracts in PBS from *Phleum pratense, Loleuin perenne, Poa pratensis, Anthoxantzn odoratum, Triticum sativum, Aveva sativa, Cynodon dactylon, Zea mays* and *Pharagmistes antralis* (Allergon AB, Vailinge, Sweden) were coated to 96-well ELISA plates (Nunc). After blocking and washing, plate-bound extract were exposed to a mouse serum pool from group I diluted 1:100 in PBS, 0.5% BSA and 0.05% Tween 20. For control purposes, a corresponding pre-immune serum pool was used. Bound IgG antibodies were detected with horseradish peroxidase-labeled sheep anti-mouse IgG antiserum (Amersham, Buckinghamshire, UK) diluted 1:1000 in 0.05% Tween 20-PBS.

6) Measurement of Cytokine Production in Spleen Cell Cultures

For determination of IL-4, IL-5 and IFN-γ production, spleen cell suspensions from immunized mice were cultured in 48-well plates (Costar, Cambridge, Mass.) with and without timothy grass pollen extract (25 µg/well) at a concentration of $5 \times 10^6$/well. Supernatants were taken 24 hours for IL-4 and IL-5 and 48 hours for IFN-γ after antigen stimulation and stored at −20° C. until analysis. Levels of IL-4 and IL-5 were measured by ELISA (Endogen, Cambridoe; Mass). The sensitivity of the tests were <5 pg/ml. IFN-γ levels were measured in 96-well plates (Nunc, Maxisorp) coated with rat anti-mouse IFN-γ (Endogen, Woburn, Mass.) at a concentration of 0.5 µg/ml carbonate buffer pH 9.6 for 6 hours at room temperature. Thereafter biotin labeled rat anti-mouse IFN-γ antibodies (Endogen) were applied at a concentration of 0.1 µg/ml, followed by peroxidase-conjugated streptavidin (1:10 000 in PBS/4% BSA; Endogen) for 30 min. For colour development TBM substrate (Chemicon, Temecula, Calif.) was used and the absorbance was measured at 450 nm. The sensitivity of the assay was <15 pg/ml. Results reflect the measured cytokine levels in pg/ml after subtraction of baseline levels of non-stimulated cultures.

7) Histopathological Analysis of Skin Sections

Skin was excised from the injection areas (1.5 cm$^2$), cut into 4 mm thick strips, fixed with 7.5% formalin, pH 7.5, and embedded in paraffin. Five µm sections were stained with hematoxylin-eosin or Giemsa.

8) ELISA Competition Assay

ELISA plates were coupled with rPhl p 5b (0.1 µg/well), blocked and washed as described for the ELISA assay above. Plates were exposed first to pooled sera of mice immunized either with CBP–rPhl p 5b (group I) or Alum-rPhl p 5b (group II) or, for control purposes, with the corresponding pre-immune serum pools diluted 1:100 over night at 4° C. After washing, the plates were incubated with sera from grass pollen allergic patients diluted 1:5. Bound human antibodies were detected with an alkaline-phosphatase conjugated mouse monoclonal antibody (PharMingen). The inhibition of allergic patients' IgE binding to rPh p 5b by the mouse immune sera was calculated using the formula 100-(OD second bleeding/OD pre-immune serum)×100.

9) Statistical Analysis

The non-parametric test Kruskal-Wallis ANOVA was used for evaluation of allergen specific antibody responses and group 5 allergen cross-reactivity between grass-species. Mann-Whitney U test was used for evaluation of mouse serum blocking of human IgE binding. $P<0.05$ was considered statistically significant.

EXAMPLE 1

CBP-Bound rPhl p 5b Induces Strong Allergen-Specific Antibody Responses

Figure 1:
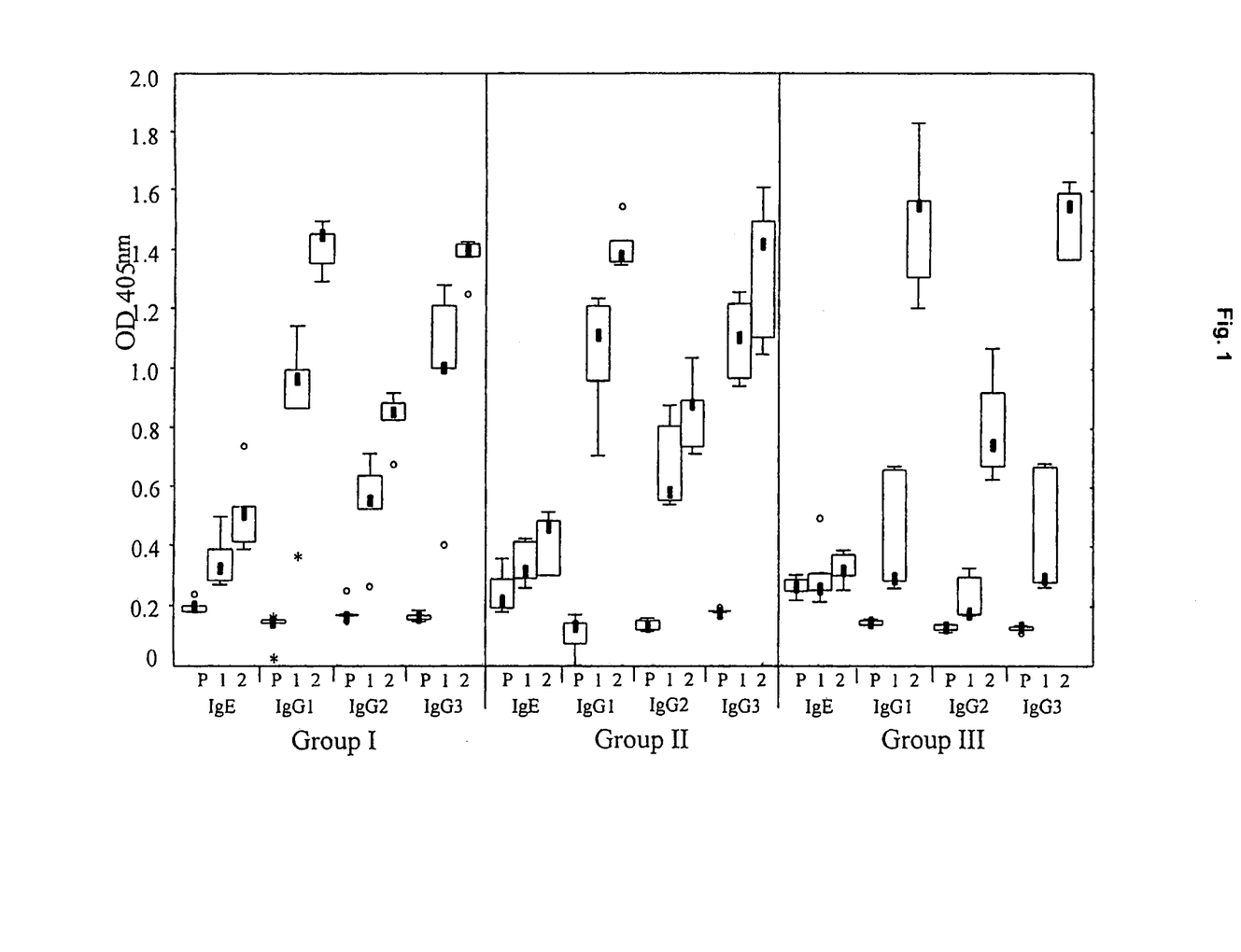
FIG. 1 shows IgE and IgG subclass responses of the three groups of immunized mice (Group I: CBP–rPhl p 5b; Group II: Alum–rPhl p 5b; and Group III: CBP+rPhl p 5b) to ELISA plate-bound rPhl p 5b.

In order to compare levels and kinetics of rPhl p S-specific antibody responses sera from all groups of mice and bleedings were analyzed separately for IgE and each IgG subclass on one ELISA plate. All three groups showed an increase of rPhl p 5b-specific antibody responses in the course of the immunizations, which peaked after the second immunization. The results of example 1 are shown in FIG. 1. FIG. 1 shows IgE and IgG subclass responses of mice to ELISA plate-bound rPhl p 5b. The optical density values (OD 405 nm) displayed on the y-axis correspond to the levels of Phl p 5b-specific IgE, $IgG_1$, $IgG_2$, and $IgG_3$ antibodies in the sera of the three mouse groups (Group I: CBP–rPhl p 5; Group II: Alum-rPhl p 5; Group III: CBP+rPhl p 5). In Group III r Phl b5b was only mixed with CBP. Results are displayed for preimmune sera (P), the first (1) and second (2) bleeding as box plots where 50% of the values are within the boxes and non-outliers between the bars. Filled squares denote median values, open circles outliers and stars extremes of each group, respectively.

Mice having received co-administered rPhl p 5b and CBP without covalent coupling (group III) showed significantly lower antibody levels after the first immunization than mice receiving CBP- or Alum-bound allergen. Both, the levels and patterns, of rPhl p 5b-specific antibody responses were similar in mice treated with CBP–rPhl p 5b, (group I) and Alum-rPhl p 5b, (group II) showing specific IgE antibody production but also specific $IgG_2$ and $IgG_3$-responses. The kinetics and magnitudes of rPhl p 5b-specific $IgG_1$ responses were similar in groups I and II.

EXAMPLE 2

Figure 2:
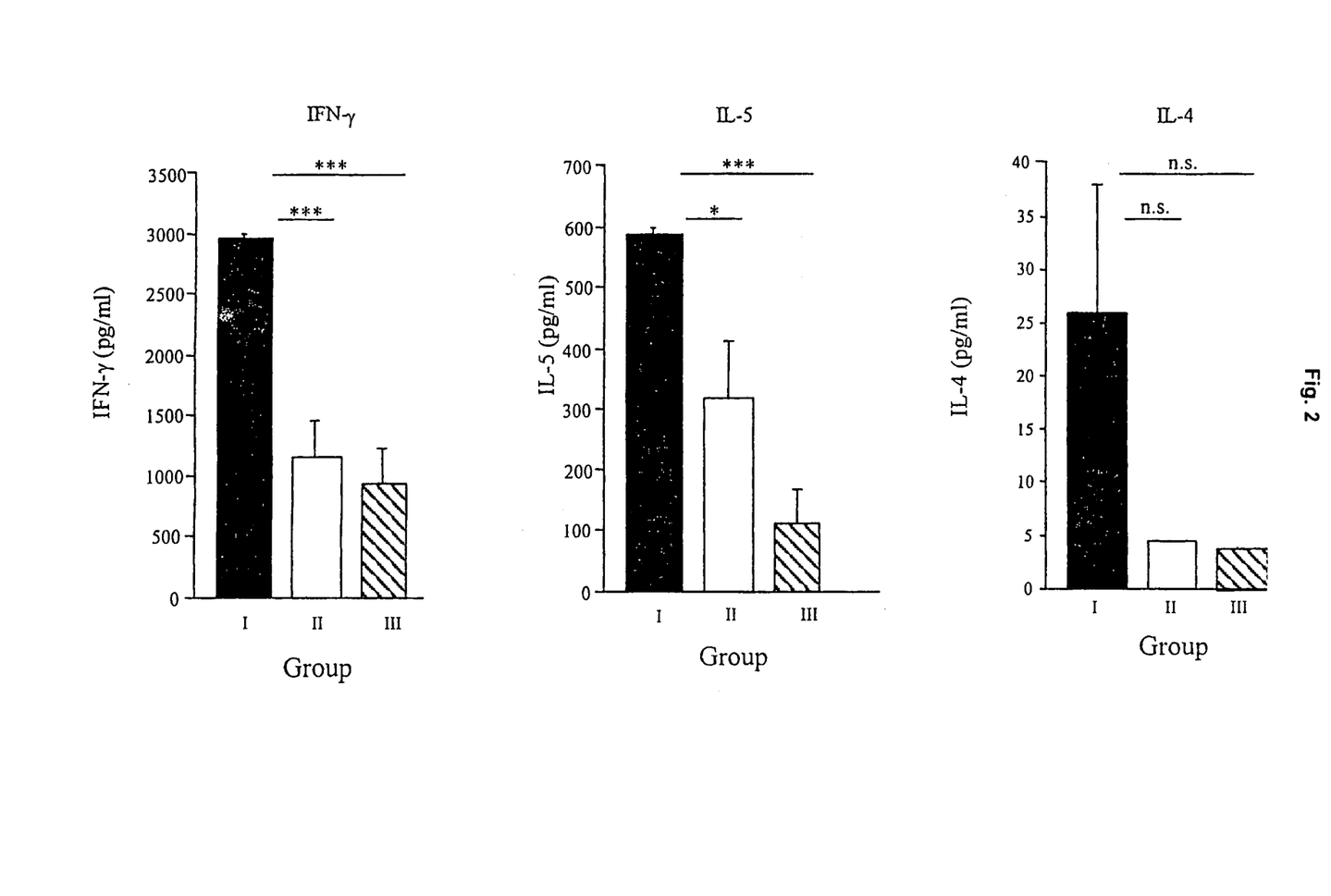
FIG. 2 shows in vitro cytokine production in antigen stimulated spleen cells of mice immunized with CBP–rPhl p 5b (Group I - black bars), Alum–rPhl p 5b (Group II - white bars) and CBP+rPhl p 5(Group III - hatched bars).

Mice Immunized with CBP-Bound rPhl p 5b Show Strong Cytokine Responses to Timothy Grass Pollen Extract The profile of IFN-γ, IL-5 and IL-4 secreted by spleen cells from mice of the three immunization groups cultivated in the presence of natural timothy grass pollen extract was similar in all three groups. FIG. 2 shows In vitro cytokine production in spleen cell cultures. IFN-γ, IL-5 and IL-4 levels were measured in supernatants of antigen stimulated spleen cells of mice which were immunized with CBP–rPhl p 5b-group I (black bars), Alum-rPhl p 5b-group II (white bars) or with CBP+rPhl p 5-group III (hatched bars). The bars indicate the mean of 5 individual values, the error bars the standard error of the mean. Mann Whitney U-Test, *$p<0.05$; ***$p<0.001$.

From the data it can be concluded that spleen cells from mice which had received CBP-conjugated rPhl p 5b mounted significantly stronger cytokine production (IFN-γ, IL-5) than spleen cells from mice treated with Alum-adsorbed rPhl p 5b. The lowest release of cytokines was found in spleen cells cultures from mice which had received a co-administration of rPhl p 5b and CBP.

EXAMPLE 3

CBP-Bound rPhl p 5b Induces Less Granulomatous Tissue Reaction than Alum-Adsorbed Allergen In order to analyse the tissue-reactions at the injection sites, skin sections were taken from the mice of group I and group II and processed for histological examination. Representative skin sections of CBP–rPhl p 5b and Alum-rPhl p 5b immunized mice were further examined. Injections sites from CBP–rPhl p 5 and Alum-rPhl p 5 immunized mice were histopathologically analyzed.

In mice receiving Alum, an overall more pronounced inflammatory reaction and additional granulomatosus responses could be seen with predominantly foam cells at the outer rim and granular debris in the center of the granuloma. The inflammatory tissue reactions of CBP–rPhl p 5b immunized mice tended to be smaller and contained less granular debris than those of the Alum-treated mice. Close ups of tissue sections of mice immunized with CBP- and Alum-bound rPhl p 5b were further analyzed. They contained a mixed cellular inflammatory infiltrate, including macrophages and lymphocytes with occasional mast cells and eosinophils at injection sites in the deep dermis, in part with granulomatous changes.

EXAMPLE 4

Figure 3:
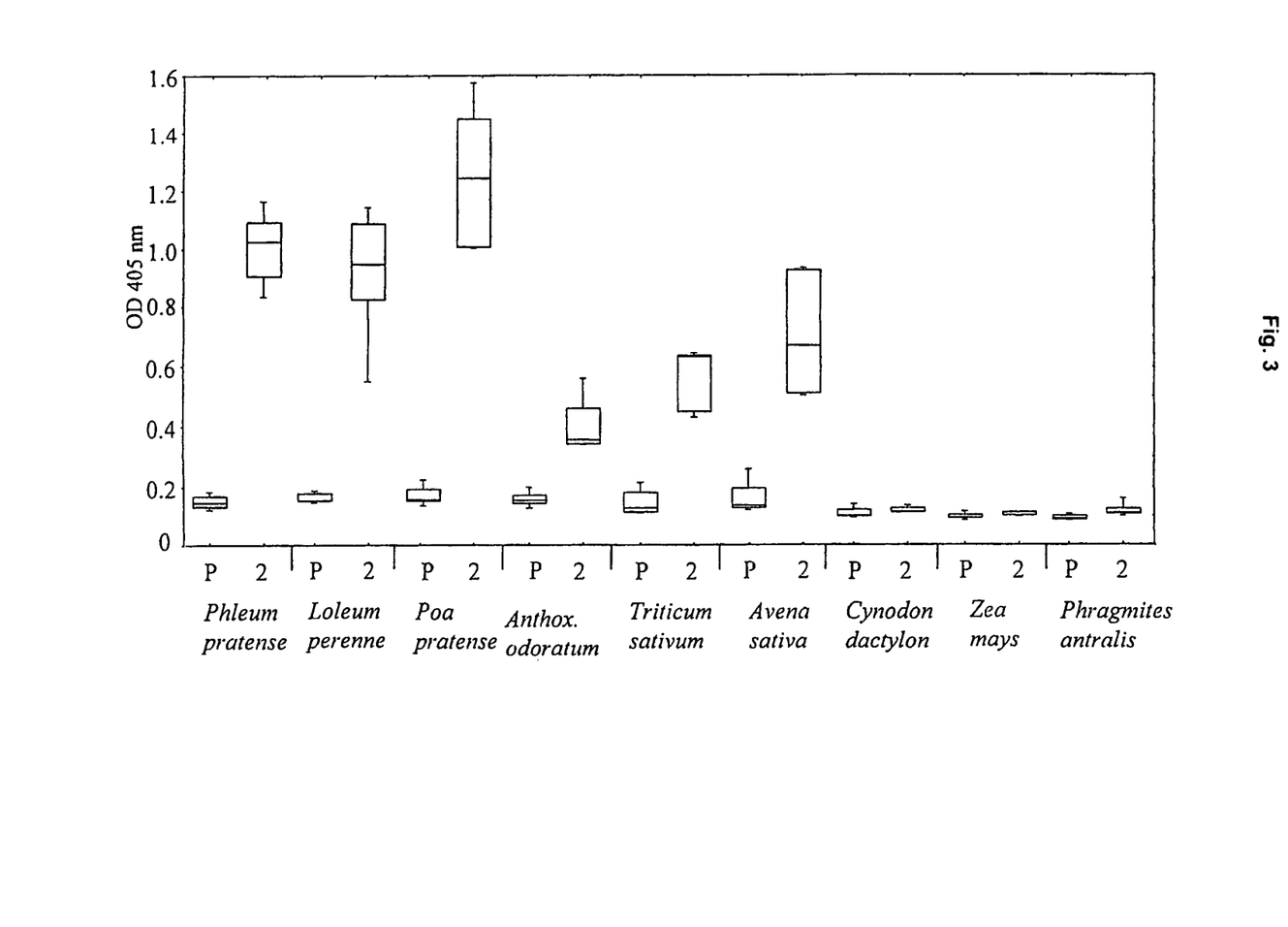
FIG. 3 depicts the results of ELISA experiments performed with a pre-immune serum pool and a serum pool containing sera from the second bleeding from CBP–rPhl p 5-immunized mice to determine the cross-reactivity of IgG antibodies with natural group 5 allergens from 9 grass species, namely *Phleum pretense, Lolium perenne, Poa pratense, Anthoxantum odoratum, Triticum sativum, Avena sativa, Cynodon dactylon, Zea mays, Phragmites antralis*. Optical density values (OD 405nm) corresponding to the serum IgG antibody levels to pollen extracts from 9 grass species (y-axis) are displayed for a serum pool collected before (P) the immunizations and during the second bleeding (2) at the x-axis.

Mice Immunized with CBP-Bound rPhl p 5b Exhibit IgG Cross-Reactivity with Natural Pollen Extracts from Grasses Containing Group 5 Allergens To study whether immunization with CBP induces IgG antibodies which cross-react with group 5 allergens from pollen of other grass species, ELISA experiments were performed with a pre-immune serum pool and a serum pool containing sera from the second bleeding. The results are shown in FIG. 3. FIG. 3 demonstrates cross-reactivity of IgG antibodies from CBP–rPhl p 5-immunized mice with natural group 5 allergens from 9 grass species. Optical density values (OD 405 nm) corresponding to the serum IgG antibody levels to pollen extracts from 9 grass species (y-axis). *Phleum pratense, Lolium perenne, Poa pratense, Anthoxantum odoratum, Triticum sativum, Avena sativa, Cynodon dactylon, Zea mays, Phragmites antralis*) are displayed for a serum pool collected before (P) the immunizations and during the second bleeding (2) at the x-axis.

rPhl p 5b-specific IgG antibodies reacted with natural group 5 allergens from timothy grass (*Phleum pratense*) and from five grass species (*Lolium perenne, Poa pratense, Anthoxanthum odoratum, Triticum sativum, Avena sativa*). The highest levels were recorded to *Poa pratense*. No IgG reactivity to pollen extracts from grasses (*Cynodon dactylon, Zea mays, Phragmites antralis*) lacking group 5-related allergens was found. The pre-immune serum pool showed no significant IgG reactivity to any of the nine grass pollen extracts.

EXAMPLE 5

Sera from Mice Immunized with CBP-Bound rPhl p 5b Inhibit the Binding of Allergic Patients' IgE to the Allergen Whether sera from mice immunized with CBP–rPhl p 5b or Alum-rPhl p 5b can inhibit the binding of grass pollen allergic patients' IgE to rPhl p 5b was studied by ELISA competition experiments. Microtitre-bound rPhl p 5b was pre-incubated with a serum pool taken on day 63 obtained from mice immunized with CBP–rPhl p 5b or Alum-rPhl p 5b and, for control purpose, with a corresponding pool of pre-immune sera and then exposed to serum IgE from nine grass pollen allergic patients.

Figure 4:
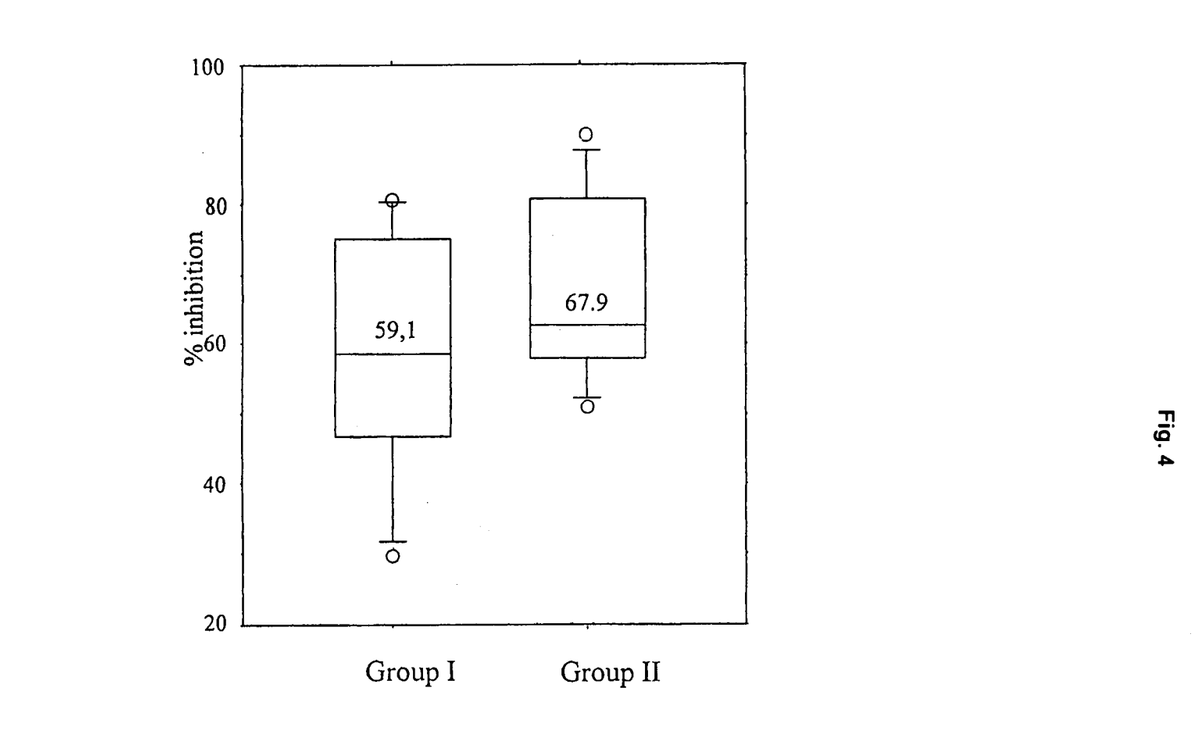
FIG. 4 depicts the results of ELISA competition experiments demonstrating the inhibition of grass pollen allergic patients' IgE binding to rPhlp 5b by murine sera, namely sera from mice immunized with CBP-rPhl p 5b (Group I) or Alum-rPhl p 5b (Group II). The percent inhibition of IgE binding determined for sera from nine grass pollen allergic patients is displayed on the y-axis. Boxes and horizontal bars denote 50% of the values and non-outlier range, respectively. Mean values are indicated and open circles denote outliers.

The results are shown in FIG. 4. FIG. 4 shows the inhibition of grass pollen allergic patients' IgE binding to rPhl p 5b by murine sera. ELISA plate-bound rPhl p 5b was preincubated with a serum pool from CBP–rPhl p 5 (Group I) or from Alum-rPhl p 5b-(Group II) immunized mice. The percentage inhibition of IgE binding determined for sera from nine grass pollen allergic patients is displayed on the y-axis. Boxes and horizontal bars denote 50% of the values and non-outlier range, respectively. Mean values are indicated and open circles denote outliers.

Sera from group I mice immunized with CBP–rPhl p 5b, inhibited allergic patients (n=9) IgE binding to rPhl p 5b from 37 to 80% (mean 59.%) whereas an inhibition between 51 to 90% (mean 67.9%) was observed with sera from group II (Alum-rPhl p 5b). Although the inhibition of IgE binding obtained with the sera from, mice treated with Alum-bound-rPhl p 5b was somewhat higher than that obtained with sera from mice of group I, no significant difference between group I and group II in terms of blocking capacity was observed ($p=0.31$, Mann-Whitney U test).

This application claims priority to EP 02008283.0 filed Apr. 22, 2002, the entirety of which is hereby incorporated by reference.

The invention claimed is:

1. A medicament for allergen-specific immunotherapy, said medicament containing a therapeutically effective amount of microparticles in a pharmaceutical formulation suitable for in vivo administration selected from the group consisting of an injectable solution, rectal foam, nasal spray, ointment and plaster, said microparticles consisting of:
   (a) a three dimensionally cross-linked agarose bead; and
   (b) at least one purified recombinant polypeptide allergen derived from plant pollen bound to said bead by means of a covalent bond between said cross-linked agarose and a reactive group of said allergen,
   wherein said medicament is capable of inducing a strong allergen-specific IgG response comparable to that of an equivalent Alum-bound allergen with less granulomatous tissue reactions as compared to said Alum-bound allergen, further wherein the microparticles have a mean diameter that ranges from 0.1 µm to 10 µm.

2. The medicament according to claim 1, wherein the bead is activated spherical agarose.

3. The medicament according to claim 1, wherein the at least one allergen is a grass pollen allergen.

4. The medicament according to claim 1, wherein the at least one allergen is a timothy grass pollen allergen.

5. The medicament according to claim 1, wherein the at least one allergen is a Phl p 5b allergen.

6. The medicament according to claim 1, wherein the microparticles have a mean diameter that ranges from 0.5 µm to 5 µm.

7. The medicament according to claim 1, wherein the microparticles have a mean diameter of 2 µm.

8. The medicament according to claim 1, wherein the bead is cyanogen bromide-activated spherical agarose and the at least one allergen is a Phl p 5b allergen.

* * * * *